(12) United States Patent
Januszko et al.

(10) Patent No.: US 11,009,561 B2
(45) Date of Patent: May 18, 2021

(54) CABLE IDENTIFICATION TESTER

(71) Applicant: Jabil Inc., St. Petersburg, FL (US)

(72) Inventors: Wieslaw Mariusz Januszko, St. Petersburg, FL (US); Hien Ly, St. Petersburg, FL (US); Jennifer Lindsey Gamboa, St. Petersburg, FL (US); Vincy Wan Sze Li, St. Petersburg, FL (US); Corey Matthew Smith, St. Petersburg, FL (US)

(73) Assignee: JABIL INC., St. Petersburg, FL (US)

( * ) Notice: Subject to any disclaimer, the term of this patent is extended or adjusted under 35 U.S.C. 154(b) by 46 days.

(21) Appl. No.: 16/360,856

(22) Filed: Mar. 21, 2019

(65) Prior Publication Data

US 2020/0300904 A1    Sep. 24, 2020

(51) Int. Cl.
*G01R 31/60* (2020.01)
*G01R 31/67* (2020.01)

(52) U.S. Cl.
CPC .............. *G01R 31/60* (2020.01); *G01R 31/67* (2020.01)

(58) Field of Classification Search
CPC ........ G01R 31/60; G01R 31/67; G01R 31/58; G01R 29/18
USPC .......................................................... 324/66
See application file for complete search history.

(56) References Cited

U.S. PATENT DOCUMENTS

| | | | |
|---|---|---|---|
| 4,837,488 A | | 6/1989 | Donahue |
| 4,937,519 A | * | 6/1990 | Fields .................... G01R 31/60 324/66 |
| 5,384,540 A | | 1/1995 | Dessel |
| 5,570,010 A | * | 10/1996 | Jin .......................... G01R 15/16 324/67 |
| 5,847,557 A | * | 12/1998 | Fincher .................. G01R 31/60 324/66 |
| 2008/0224686 A1 | * | 9/2008 | Boucher ................ G01R 31/67 324/66 |
| 2009/0323786 A1 | * | 12/2009 | Buer ........................ H04B 1/74 375/220 |
| 2011/0152962 A1 | * | 6/2011 | Behm .................. A61N 1/3706 607/10 |

(Continued)

FOREIGN PATENT DOCUMENTS

| | | |
|---|---|---|
| JP | H0526940 A | 2/1993 |
| JP | H0552895 A | 3/1993 |

OTHER PUBLICATIONS

International Search Report; International Application No. PCT/US2020/023323; International Filing Date: Mar. 18, 2020; dated Jul. 17, 2020; 5 pages.

(Continued)

*Primary Examiner* — Christopher P McAndrew
(74) *Attorney, Agent, or Firm* — Cantor Colburn LLP (57) ABSTRACT

A method of identifying opposing ends of a cable within a cabling assembly having a plurality of cables. The method includes transmitting a signal to a first end of a cable of the plurality of cables, receiving the signal at a second end of the cable of the plurality of cables, transmitting an output signal from a connector operably coupled to the second end of the cable of the plurality of cables to a processor. The connector is one of a plurality of connectors. The method additionally includes identifying using an indicator device the connector of the plurality of connectors that is operably coupled to the second end of the cable.

18 Claims, 5 Drawing Sheets

(56) References Cited

U.S. PATENT DOCUMENTS

| | | | |
|---|---|---|---|
| 2013/0110433 A1* | 5/2013 | Gotschall | G01R 31/58 |
| | | | 702/64 |
| 2015/0048835 A1* | 2/2015 | Lee | G01R 31/50 |
| | | | 324/414 |
| 2015/0241255 A1* | 8/2015 | Zhang | G01F 25/0007 |
| | | | 73/861.12 |

OTHER PUBLICATIONS

Written Opinion of the International Searching Authority; International Application No. PCT/US2020/023323; International Filing Date: Mar. 18, 2020; dated Jul. 17, 2020; 7 pages.

* cited by examiner

CABLE IDENTIFICATION TESTER

BACKGROUND OF THE INVENTION

Field of the Invention

Exemplary embodiments disclosed herein relate generally to a cabling assembly, and more particularly, to a test device and method of use thereof for detecting and identifying corresponding ends of a cable within a cabling assembly.

Description of the Background

Electrical transmission devices, such as electrode catheters, typically consist of a central core of wires or cables terminating at a distal end with one or more electrodes and at the proximal end with connector pins. Prior to affixing the connector to the proximal ends of the cables, an operator must identify each distinct channel within the catheter by identifying the two ends of each cable. Proper identification is critical because the electrical transmission device may directly affect the health and safety of a person relying on the operation of the device.

Currently, the interconnected and opposed ends of a cable of such an electrical transmission device are identified using a multimeter. The identification process is continuously repeated (largely by trial and error) until the measured resistance indicates that the multimeter is connected to opposed ends of the same cable. Accordingly, existing methods of identification are time consuming.

SUMMARY OF THE INVENTION

According to an embodiment, a method of identifying opposing ends of a cable within a cabling assembly having a plurality of cables. The method includes transmitting a signal to a first end of a cable of the plurality of cables, receiving the signal at a second end of the cable of the plurality of cables, transmitting an output signal from a connector operably coupled to the second end of the cable of the plurality of cables to a processor. The connector is one of a plurality of connectors. The method additionally includes identifying using an indicator device the connector of the plurality of connectors that is operably coupled to the second end of the cable.

In addition to one or more of the features described above, or as an alternative, in further embodiments transmitting the signal to the first end of the cable includes directly contacting the first end of the cable with a connector.

In addition to one or more of the features described above, or as an alternative, in further embodiments the connector is a probe.

In addition to one or more of the features described above, or as an alternative, in further embodiments receiving the signal at the second end of the cable further comprises receiving the signal at an electrode operably coupled to the cable, the electrode being positioned near the second end of the cable.

In addition to one or more of the features described above, or as an alternative, in further embodiments comprising transmitting the signal from the electrode to the connector.

In addition to one or more of the features described above, or as an alternative, in further embodiments comprising transmitting a signal to a first end of a second cable of the plurality of cables, receiving the signal at a second end of the second cable, transmitting an output signal from a second connector operably coupled to the second end of the second cable to the processor, and identifying on the indicator device the second connector that is operably coupled to the second end of the second cable.

In addition to one or more of the features described above, or as an alternative, in further embodiments transmitting the signal to the first end of the cable and transmitting the signal to the first end of the second cable occurs sequentially.

In addition to one or more of the features described above, or as an alternative, in further embodiments transmitting the signal to the first end of the cable includes directly contacting the first end of the cable with a probe and transmitting the signal to the first end of the second cable includes decoupling the probe from the cable and directly contacting the first end of the second cable with the probe.

In addition to one or more of the features described above, or as an alternative, in further embodiments transmitting the signal to the first end of the cable and transmitting the signal to the first end of the second cable occurs sequentially.

In addition to one or more of the features described above, or as an alternative, in further embodiments identifying on the indicator device the connector that is operably coupled to the second end of the cable and identifying on the indicator device the second connector that is operably coupled to the second end of the second cable occur simultaneously.

According to another embodiment, a system for identifying opposing ends of a cable within a cabling assembly having a plurality of cables includes a processor connectable to a first end of a cable of the plurality of cables. A plurality of connectors is operably coupled to the processor and the plurality of connectors is connectable to a second end of each of the plurality of cables, respectively. An input/output device is operably coupled to the processor. The input/output device includes an indicator device operable to display information identifying which connector of the plurality of connectors is associated with the first end of the cable.

In addition to one or more of the features described above, or as an alternative, in further embodiments the system further comprises a connector operably coupled to the processor, wherein the connector is positionable in direct contact with the first end of the cable.

In addition to one or more of the features described above, or as an alternative, in further embodiments the connector is a probe.

In addition to one or more of the features described above, or as an alternative, in further embodiments the connector includes a plurality of terminals, each of the plurality of terminals being connectable to a first end of one of the plurality of cables.

In addition to one or more of the features described above, or as an alternative, in further embodiments at least a portion of the system is positioned within a housing, and together the housing and the system form a portable identification device.

In addition to one or more of the features described above, or as an alternative, in further embodiments the input/output device is arranged at an exterior of the housing.

In addition to one or more of the features described above, or as an alternative, in further embodiments the input/output device includes at least one of a display and one or more light emitting devices.

In addition to one or more of the features described above, or as an alternative, in further embodiments the housing includes an opening for receiving the second end of each of the plurality of cables and the plurality of connectors are mounted directly adjacent the opening.

In addition to one or more of the features described above, or as an alternative, in further embodiments the cabling assembly is an electrode catheter.

In addition to one or more of the features described above, or as an alternative, in further embodiments the cabling assembly is a coaxial cable.

DETAILED DESCRIPTION

A detailed description of one or more embodiments of the disclosed apparatus and method are presented herein by way of exemplification and not limitation with reference to the Figures.

Figure 1:
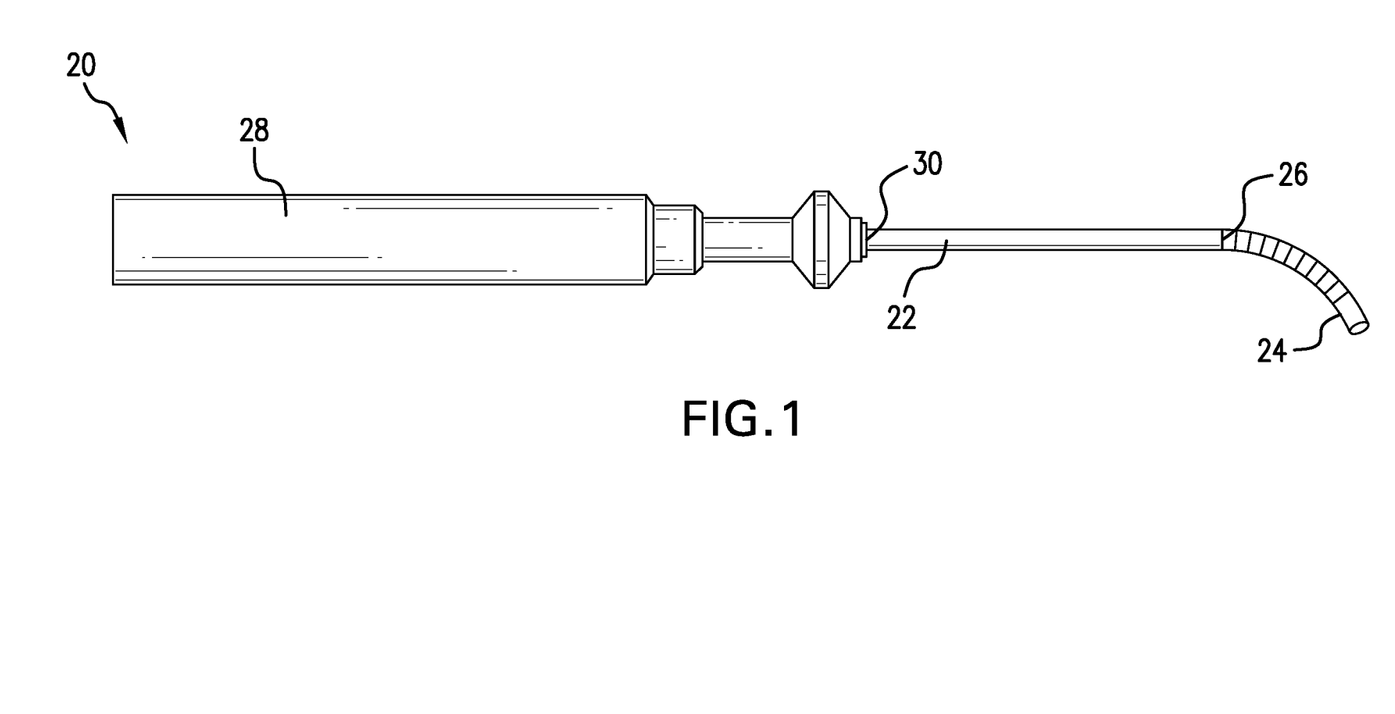
FIG. 1 is a schematic drawing of an example of a cabling assembly according to an embodiment.
Figure 2:
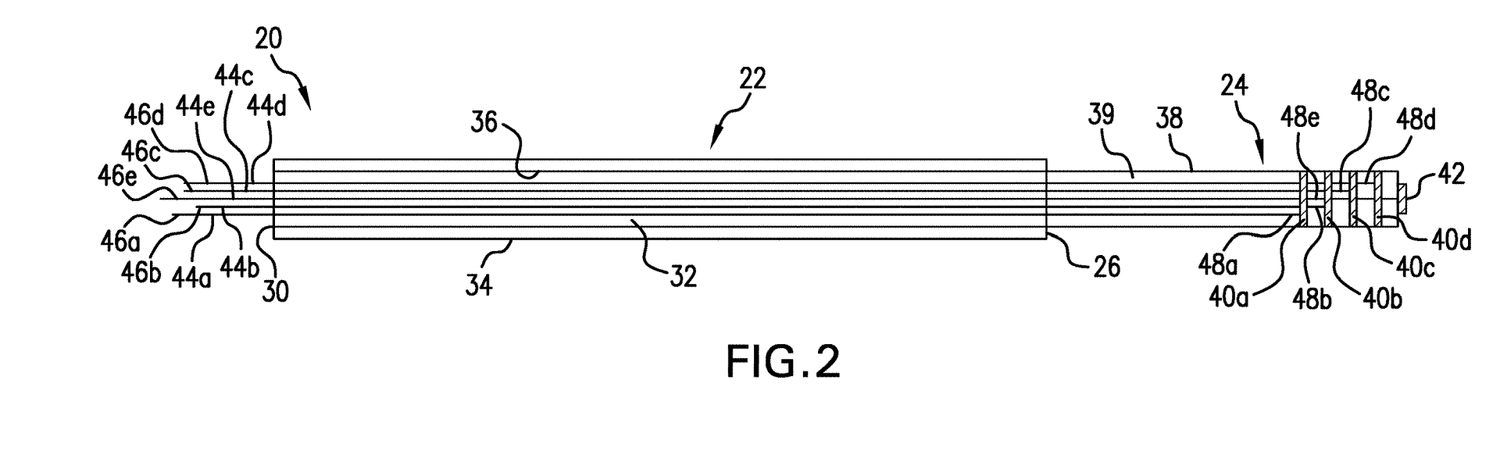
FIG. 2 is a cross-sectional view of a cabling assembly according to another embodiment.

With reference now to FIGS. 1 and 2, an example of a cabling assembly 20 is illustrated. In the illustrated, non-limiting embodiment, the cabling assembly 20 is an electrode catheter including an elongated body 22 and a tip section 24 arranged at a distal end 26 of the body 22. In an embodiment, best shown in FIG. 1, a control handle 28 is located at the proximal end 30 of the body 22. The elongated body 22 has a tubular construction defining a single, central or axial lumen 32. The body 22 is formed from a flexible, for example bendable, electrically insulating material that is substantially non-compressible along its length. The body 22 may have any suitable construction and may be made of any suitable material. In an embodiment, the body 22 includes an outer wall 34 formed from a polyurethane material and contains an imbedded braided stainless steel mesh (not shown) that increases the torsional stiffness of the body 22. The interior of the body 22 includes a stiffening tube 36, such as formed from a nylon material for example, the interior surface of which forms the central lumen 32. An outer diameter of the stiffening tube 36 may be about equal to or slightly smaller than the inner diameter of the outer wall 34. The stiffening tube 36 may be fixedly attached to the outer wall 34 in any suitable manner.

The tip section 24 of the cabling assembly 20 includes a short section of flexible tubing 38 having one or more lumens 39 defined therein. The tip section 24 may be attached to the distal end 26 of the body 22, with a suitable adhesive material (not shown), such as glue for example. In an embodiment, the tip section 24 includes a plurality of electrodes, such as ring electrodes 40a-40d spaced apart from one another and/or a tip electrode 42 for example. An outer diameter of the ring electrodes 40a-40d may be about the same as the outer diameter of the flexible tubing 38 so that the electrodes 40a-40d form a smooth, continuous surface with the external surface of the flexible tubing 38. Alternatively, the electrodes may have an outer diameter slightly larger than the diameter of the flexible tubing 38 so that the electrodes 40a-40d protrude slightly from the surface of the flexible tubing 38.

With specific reference to FIG. 2, the cabling assembly 20 additionally includes a plurality of lead cables or wires 44. The lead cables, shown as 44a-44e, extend through both a lumen 39 of the tip section 24 and through the central lumen 32 of the body 22 such that a proximal end 46a-46e of each of the lead cables extends 44a-44e beyond the proximal end 30 of the body 22. In embodiments where the cabling assembly 20 includes a control handle 28, as shown in FIG. 1, a proximal end 46a-46e of each of the plurality of lead cables 44a-44e is received within and/or extends through the control handle 28 for coupling to a connector (not shown) suitable for use with a monitor, energy source, or other suitable device.

Each of the plurality of electrodes 40a-40d and 42 is electrically connected to a distal end 48a-48e of a separate lead cable 44a-44e of the plurality of lead cables 44a-44e by any suitable technique. Although five lead cables 44a-44e are shown in the illustrated, non-limiting embodiment, it should be understood that embodiments having any number of lead cables 44, such as between two and twenty lead cables, or more than twenty lead cables are also contemplated herein. Further, because each lead cable is coupled to a distinct electrode, it should be understood that a cabling assembly 20 having any number and type of electrodes, such two or more ring electrodes for example, is within the scope of the disclosure.

The electrode catheter illustrated and described is intended as an example only. It should be understood that other configurations of an electrode catheter having multiple lead cables are contemplated herein within the scope of the term "cabling assembly." In addition, other cabling assemblies, such as a coaxial cable, or a cable bundle having two or more partially sheathed cables are also within the scope of the disclosure.

Prior to affixing a connector or control handle 28 to the proximal ends 46a-46e of the lead cables 44a-44e, the association between the proximal end 46a-46e of each lead cable 44a-44e, respectively and a distal end 48a-48e of each lead cable 44a-44e. Because the distal ends 48a-48e of the lead cables 44a-44e are hidden within a lumen 39 of the tip section 24, and because the plurality of lead cables 44a-44e are substantially identical (i.e. no distinguishing marks), the lead cable 44a-44e and electrode 40a-40d, 42 pairs require identification.

Figure 3:
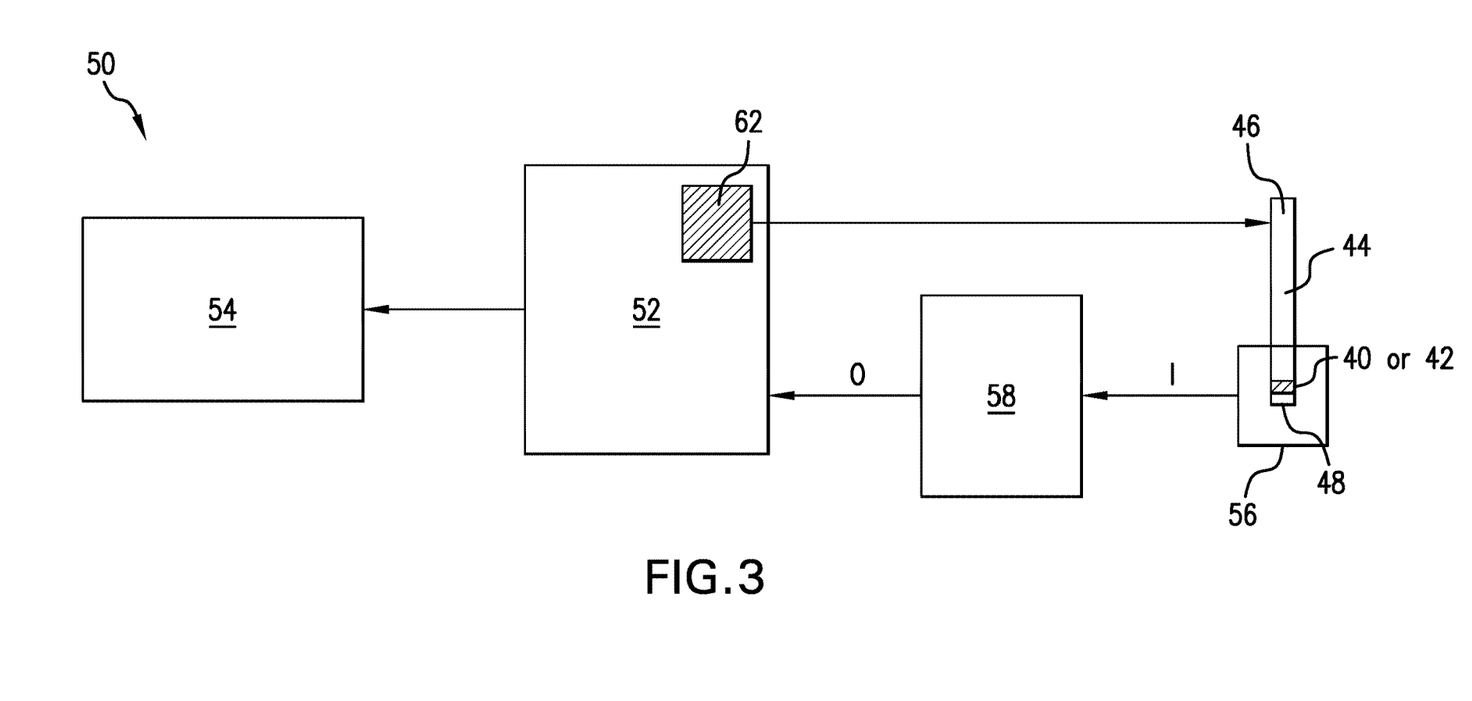
FIG. 3 is a schematic diagram of a computing system operable to identify a relationship between a proximal end of a cable and a distal end of a cable of a cabling assembly.

With reference now to FIG. 3, a schematic diagram of an example of a computing system 50 operable to identifying an electrode 40 or 42 associated with an exposed end of a cable 44, such as electrode 40a-40d, 42 of the lead cables 44a-44e of the cabling assembly 20 for example, is illustrated according to an embodiment. As shown, the computing system 50 includes a processor 52. The processor 52 may be any type of processor, including a general-purpose processor, a digital signal processor, a microcontroller, an application specific integrated circuit (ASIC), a field programmable grid array (FPGA), or the like. In an embodiment, the processor 52 may include one or more image processors for processing the associated data from the acquisition devices using one or more processing algorithms to produce one or more processed signals.

The computing system 50 additionally includes one or more input/output (I/O) devices 54 operably coupled to the processor 52. In an embodiment, the at least one I/O device 54 is an indicator for providing identifying information to a user regarding the electrode 40, 42, and therefore the distal end 48, associated with a proximal end 46 of a cable 44 of the cabling assembly 20. Examples of such indicators include, but are not limited to a display screen, light emitting diode, or speaker for example. Alternatively, or in addition, the I/O device 54 may be configured to provide an interface to allow a user to interact with the computing system 50.

At least one connector 56 is electrically connectable to a distal end of cable 44 of the cabling assembly. In an embodiment, the at least one connector 56 is a spring loaded connector and is configured to electrically couple to an electrode 40, 42 of the cabling assembly 20. In embodiments where the cabling assembly 20 includes a plurality of lead cables 44, and therefore a plurality of electrodes 40, 42, the computing system 50 includes a plurality of connectors 56, and each connector 56 is configured to couple to a single electrode associated with one of the plurality of cables 44.

In an embodiment, the computing system 50 includes at least one multiplexer having a programmable set of inputs and outputs, illustrated schematically at 58. The at least one multiplexer 58 is operably coupled not only to the processor 52, but also each of the plurality of connectors 56. Each of the plurality of connectors 56 is operable to provide an input signal I to the multiplexer 58 and a selected one of the input signals I is provided to the processor 52 as an output signal O.

Figure 4A:
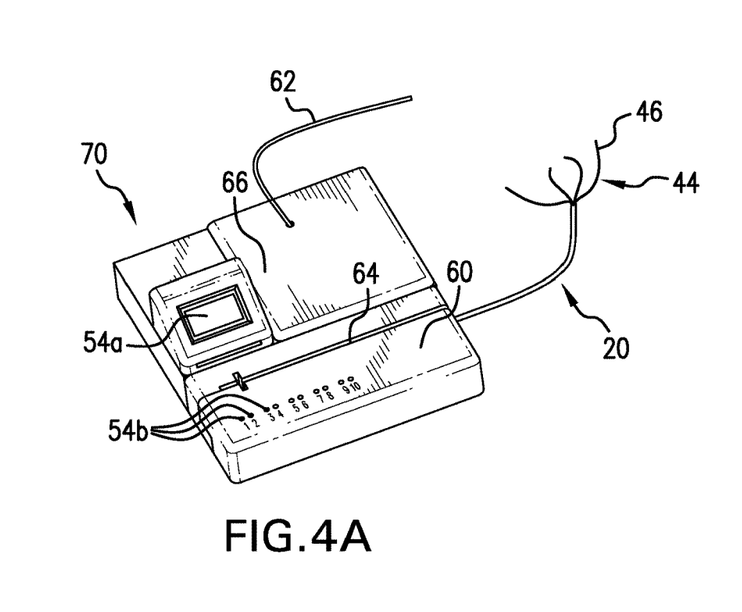
FIG. 4A is a perspective view of an identification device including computing system operable to identify a relationship between a proximal end of a cable and a distal end of a cable of a cabling assembly according to an embodiment.
Figure 4B:
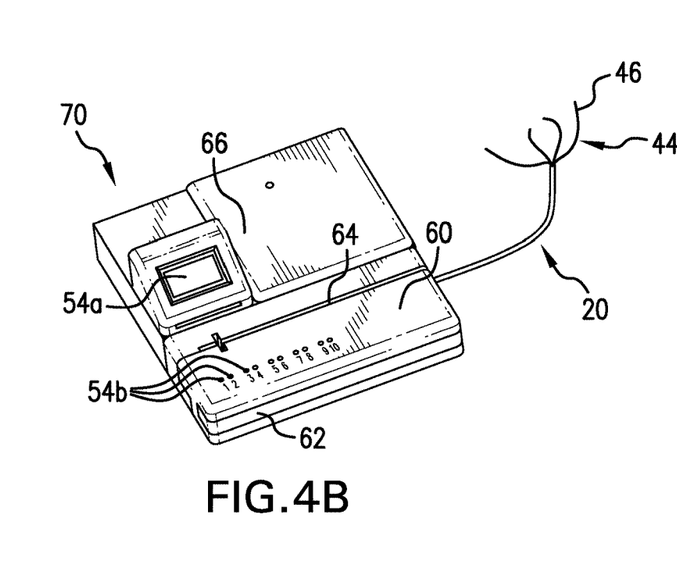
FIG. 4B is a perspective view of an identification device including computing system operable to identify a relationship between a proximal end of a cable and a distal end of a cable of a cabling assembly according to an embodiment.

With reference now to FIG. 4, in an embodiment, the computing system 50 is wholly contained by a housing 60 to provide a portable device 70 capable of identifying the cables within a cable bundle or cabling assembly 20. The housing 60 may be formed from any suitable material, such as plastic for example. In the illustrated, non-limiting embodiment, a connection mechanism 62 operably coupled to the processor 52 may be movable or fixed relative to the exterior of the housing 60. In the illustrated, non-limiting embodiment of FIG. 4, the connection mechanism 62 includes a probe or a conductor that may selectively contact the proximal end 46 of each cable 44 of a cabling assembly 20 individually. In another embodiment, the connection mechanism 62 includes a plurality of terminals, and each terminal is configured to receive and electrically connect to the proximal end of a corresponding cable 44 of the cabling assembly 20. Accordingly, in embodiments where the connection mechanism 62 includes a plurality of terminals, the processor 52 is arranged in communication with each of the plurality of cables 44 of the cabling assembly 20.

An opening 64 is formed in a portion of the housing 60 for receiving the tip section 24 of the cabling assembly 20. In an embodiment, the plurality of connectors 56 configured to connect to the plurality of electrodes 40, 42 of the cabling assembly 20 are mounted directly adjacent the opening 64 such that when the tip section 24 is installed within the opening 64, a connector 56 is electrically coupled to each of the plurality of electrodes 40, 42 of the tip section 24.

Further, the at least one indicator I/O device 54 of the computing system 50 is exposed at an exterior of the housing 60. In the illustrated, non-limiting embodiment, the at least one I/O device includes a display screen 54a mounted at an upper surface 66 of the housing 60. Alternatively, or in addition, a plurality of light emitting devices 54b, such as light emitting diodes (LEDs) for example, may be mounted so as to be visible at a surface of the housing 60. In such embodiments, each of the light emitting devices 54 may be associated with one of the connectors 56. It should be understood that the configuration of the device 70 illustrated and described herein is intended as an example only.

During operation of the device 70, the processor 52 is selectively coupled to one or more of the plurality of cables 44 of the cabling assembly 20. In an embodiment, this coupling is performed by directly contacting the proximal end 46 of a cable 44 with the connection mechanism 62. Via this contact, an electrical signal generated by the processor 52 is transmitted or communicated to the cable 44. The electrical signal is received by the electrode 40, 42 associated with the cable 44, and also by the connector 56 coupled to the electrode 40, 42. In response, the connector 56 will generate a signal, which is returned to the processor 52 to complete the transmission circuit. The processor 52 determines which connector 56 of the plurality of connectors 56 generated the signal, and sends a signal to the I/O device 54 to indicate identifying information of the connector 56 and/or electrode 40, 42 associated with the cable 44 that was contacted. For example, if the electrode 40, 42 coupled to connector "4" of the device 70 and computing system 50 communicates a signal to the processor 52 in response to the signal output therefrom, the I/O device may display a number "4" on the display screen 54a, and/or the LED 54b associated with the fourth connector, such as via reference numerals for example, may illuminate.

Alternatively, the proximal end 46 of multiple cables 44 of the cabling assembly 20 may be electrically connected to the processor 52 simultaneously via the connection mechanism 62. An electrical signal output from the processor 52 is therefore automatically communicated to each of the plurality of cables 44 via the connection mechanism 62. These electrical signals may be communicated sequentially, or alternatively, concurrently. The electrical signals are transmitted via each cable 44 to a corresponding electrode 40, 42 located at the distal end 48 of the cables 44. The electrical signal is received by the electrode 40, 42 associated with a cable 44, and also by the connector 56 coupled to the electrode 40, 42, respectively.

Figure 5A:
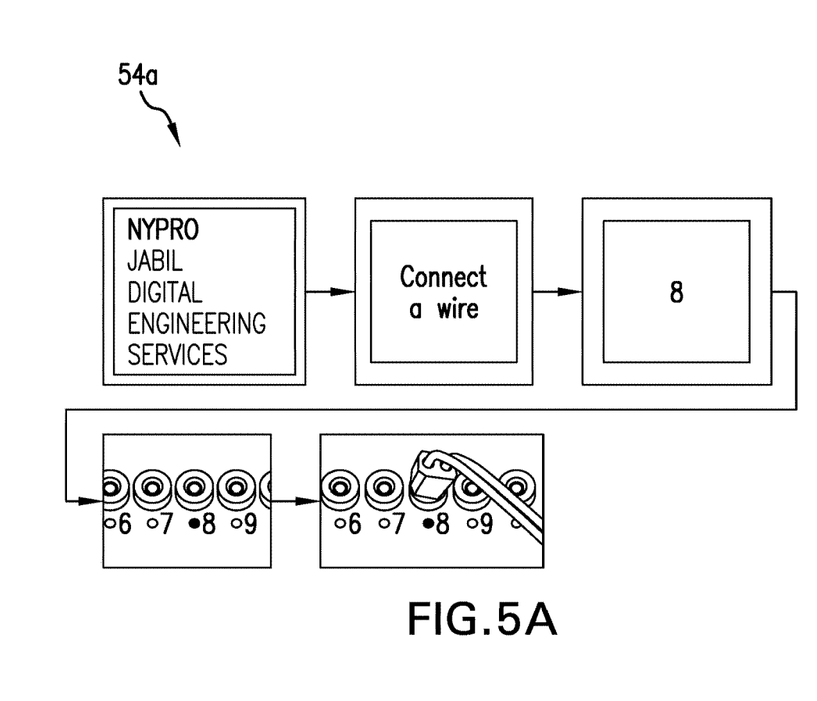
FIG. 5A is an example of a display of an input/output device associated with an identification device according to an embodiment.
Figure 5B:
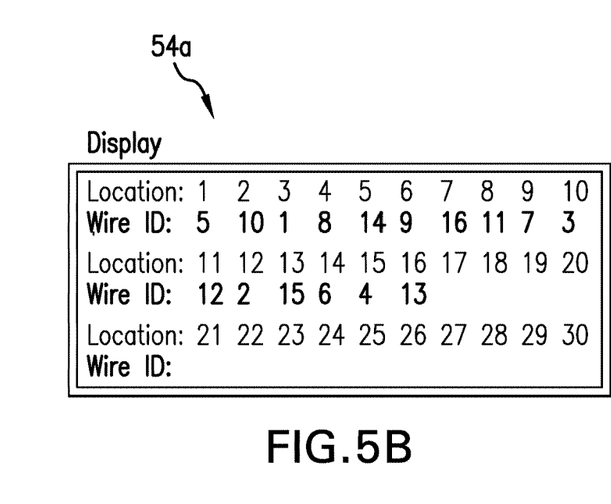
FIG. 5B is another example of a display of an input/output device associated with an identification device according to an embodiment.

As previously described, the connector 56 will generate a signal, which is returned to the processor 52 to complete the transmission circuit. In embodiments where a connection mechanism 62 is coupled to multiple cables 44 of the cabling assembly 20 simultaneously, the computing system 50 likely includes one or more multiplexers for organizing the input signals received from each of the connectors. In such embodiments, the inputs signals from each of the connectors 56 are selectively provided to the processor 52 from the multiplexer 58 as an output signal when prompted. The processor 52 may coordinate the identification information for each of the plurality of cables 44 of the cabling assembly 20 and display such information to a user simultaneously, as shown in FIG. 5. After identifying the ends of each cable 44, the first end 46a-46e of each cable 44a-44e may be labeled, coded, or otherwise marked to indicate which cable 44a-44e corresponds to which electrode 40a-40d, 42 of the cabling assembly 20. The proximal ends 46a-46e may then be affixed to a connector (not shown), such as via a soldering or welding operation for operation of the cabling assembly 20.

A portable identification device 70 having a computing system 50 as described herein allows for efficient identification of opposed ends of one or more cables within a cabling assembly 20. As previously described, the identification device may be suitable for use with any type of cabling assembly having a plurality of cables, where the cables are absent any identifying marks or indicia bundled together.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A method of identifying opposing ends of a cable within a cabling assembly having a plurality of cables, the method comprising:
    providing a plurality of cables, each cable having an exposed first end and a hidden second end connected to an electrode;
    coupling the electrode associated with each cable to a respective connector of a plurality of connectors,
    transmitting a signal from a processor to a first end of a cable of the plurality of cables;
    receiving the signal at the electrode connected to the cable of the plurality of cables;
    transmitting an output signal from the connector operably coupled to the electrode connected to the cable of the plurality of cables to the processor; and
    identifying, using an indicator device operably coupled to the processor, the connector of the plurality of connectors that is coupled to the electrode associated with the second end of the cable.

2. The method of claim 1, wherein transmitting the signal to the first end of the cable includes directly contacting the first end of the cable with a connector.

3. The method of claim 2, wherein the connector is a probe.

4. The method of claim 1, further comprising transmitting the signal from the electrode to the connector.

5. The method of claim 1, further comprising:
    transmitting a signal from the processor to a first end of a second cable of the plurality of cables;
    receiving the signal at a second electrode coupled to the second end of the second cable;
    transmitting an output signal from a second connector operably coupled to the second electrode connected to the second cable to the processor; and
    identifying, using the indicator device, the second connector of the plurality of connectors that is coupled to the second electrode associated with the second end of the second cable.

6. The method of claim 5, wherein transmitting the signal to the first end of the cable and transmitting the signal to the first end of the second cable occurs sequentially.

7. The method of claim 6, wherein transmitting the signal to the first end of the cable includes directly contacting the first end of the cable with a probe and transmitting the signal to the first end of the second cable includes decoupling the probe from the cable and directly contacting the first end of the second cable with the probe.

8. The method of claim 5, wherein transmitting the signal to the first end of the cable and transmitting the signal to the first end of the second cable occurs sequentially.

9. The method of claim 5, wherein identifying, using the indicator device, the connector that is operably coupled to the electrode associated with the cable and identifying, using the indicator device, the second connector that is coupled to the second electrode associated with the second cable occur simultaneously.

10. A system for identifying opposing ends of a cable within a cabling assembly having a plurality of cables, the system comprising:
    a processor connectable to a first end of a cable of the plurality of cables;
    a plurality of connectors operably coupled to the processor, the plurality of connectors being connectable to a second end of each of the plurality of cables, respectively; and
    an input/output device operably coupled to the processor, wherein the input/output device includes an indicator device operable to display information identifying which connector of the plurality of connectors is associated with the first end of the cable;
    wherein the cabling assembly is an electrode catheter.

11. The system of claim 10, wherein the system further comprises a connector operably coupled to the processor, wherein the connector is positionable in direct contact with the first end of the cable.

12. The system of claim 11, wherein the connector is a probe.

13. The system of claim 11, wherein the connector includes a plurality of terminals, each of the plurality of terminals being connectable to a first end of one of the plurality of cables.

14. The system of claim 10, wherein at least a portion of the system is positioned within a housing, and together the housing and the system form a portable identification device.

15. The system of claim 14, wherein the input/output device is arranged at an exterior of the housing.

16. The system of claim 15, wherein the input/output device includes at least one of a display and one or more light emitting devices.

17. The system of claim 14, wherein the housing includes an opening for receiving the second end of each of the plurality of cables and the plurality of connectors are mounted directly adjacent the opening.

18. The system of claim 10, wherein the cabling assembly is a coaxial cable.

* * * * *